United States Patent [19]
Eastman et al.

[11] Patent Number: 5,237,122
[45] Date of Patent: Aug. 17, 1993

[54] ALKYLATION CATALYST REGENERATION

[75] Inventors: Alan D. Eastman; Robert B. Eldridge; Richard L. Anderson, all of Bartlesville, Okla.; David P. Mann, Katy, Tex.

[73] Assignee: Phillips Petroleum Company, Bartlesville, Okla.

[21] Appl. No.: 935,089

[22] Filed: Aug. 24, 1992

[51] Int. Cl.$^5$ .......................... C07C 2/56; C07C 2/58; C07C 315/00; B01J 20/34

[52] U.S. Cl. .................................... 585/709; 585/724; 585/730; 585/732; 585/901; 585/835; 585/868; 568/28; 502/22

[58] Field of Search ............... 585/709, 724, 730, 732, 585/901, 835, 868; 568/28; 502/22

[56] References Cited

U.S. PATENT DOCUMENTS

| | | | |
|---|---|---|---|
| 3,795,712 | 3/1974 | Torck et al. | 260/671 C |
| 4,014,953 | 3/1977 | Brown, Jr. | 260/683.48 |
| 4,024,203 | 5/1977 | Torck et al. | 260/683.15 A |
| 4,189,616 | 2/1980 | Liebert | 585/701 |
| 4,507,506 | 3/1985 | Shioyama | 568/401 |
| 4,663,026 | 5/1987 | Louie et al. | 208/262 |
| 4,861,447 | 8/1989 | Blytas et al. | 204/181.8 |
| 4,897,182 | 1/1990 | Maier et al. | 208/321 |

Primary Examiner—Anthony McFarlane
Assistant Examiner—Nhat D. Phan
Attorney, Agent, or Firm—Charles W. Stewart

[57] ABSTRACT

Disclosed is a process for removing acid soluble oils, produced as an undesirable by-product of an HF catalyzed alkylation reaction, from a liquid containing a sulfone compound. The process includes the use of water to induce the formation of the two immiscible liquid phases of ASO and sulfone with water. The two immiscible phases can subsequently be separated from each other.

19 Claims, 1 Drawing Sheet

ALKYLATION CATALYST REGENERATION

The present invention relates to the regeneration of a catalyst composition utilized in a hydrocarbon conversion process. More particularly, the invention relates to the regeneration of a catalyst mixture, comprising a sulfone compound and a hydrogen halide compound, utilized in the alkylation of olefin hydrocarbons by isoparaffin hydrocarbons.

BACKGROUND OF THE INVENTION

It has recently been discovered that a mixture, comprising a sulfone compound and a hydrogen halide compound, is an effective catalyst for use in the alkylation of olefin hydrocarbons by isoparaffin hydrocarbons to produce an alkylate reaction product, or alkylate. This discovery has been disclosed or claimed, or both, in several patent applications such as U.S. application Ser. No. 07/877,336 of Abbott and Randolph, filed May 1, 1992, and U.S. application Ser. No. 07/877,338 of Abbott et al, filed May 1, 1992. The alkylate reaction product generally contains hydrocarbons having seven or more carbon atoms, and it is a highly desirable gasoline blending component because of its high octane value as a motor fuel.

While a process which utilizes a catalyst composition comprising a sulfone component and a hydrogen halide component produces an alkylate product of very high quality, one side effect from using such a process in the production of alkylate is the formation of certain polymeric reaction by-products such as those referred to as acid-soluble oils, or ASO. These polymeric reaction by-products are referred to as acid-soluble oils because they are soluble in the catalyst utilized in the alkylation process; and thus remain in the catalyst phase when the alkylate product resulting from the contact of a hydrocarbon mixture with an alkylation catalyst is separated from the alkylation catalyst. In an alkylation process which continuously separates the catalyst phase from the alkylation reaction product for reuse in the process reaction zone, there is a buildup of ASO in the catalyst. Over time the ASO concentration will reach unacceptable concentration levels if not removed. A low concentration of ASO in the alkylation catalyst comprising a sulfone component and a hydrogen halide component is believed to have a beneficial effect upon the alkylation process or its product. However, higher concentrations of ASO in the alkylation catalyst have an adverse effect upon the catalyst activity and the final alkylate end-product. An ASO concentration in the alkylation catalyst that exceeds certain acceptable limits will result in lowering the octane of the alkylate end-product with incremental increases in the ASO concentration causing incremental decreases in the alkylate octane.

In conventional alkylation processes that use hydrogen fluoride (HF) as a catalyst, as opposed to the use of the aforementioned novel catalyst comprising a sulfone component and a hydrogen halide component, there are certain known methods used to remove the ASO from the HF catalyst used in a continuous alkylation process. Particularly, enough of a portion of the HF catalyst that is utilized in the alkylation process is treated, or regenerated, so as to remove an amount of ASO at a rate that approximates the rate of accumulation of ASO in the alkylation catalyst. This is done by passing a portion of the HF catalyst to a stripping vessel whereby the HF is stripped from the ASO by means of a vaporous hydrocarbon such as isobutane with the HF passing as a part of the vaporous overhead stream from the stripping vessel and the ASO passing as a bottoms stream from the stripping vessel for further processing.

While the conventional alkylation catalyst regeneration techniques have worked well in the regeneration of the conventional HF catalyst, conventional means cannot be used to regenerate an alkylation catalyst mixture which includes a sulfone component. This is because the boiling range of ASO overlaps the boiling temperatures of certain sulfones such as sulfolane. Therefore, simple distillation techniques as are used to separate HF from ASO cannot be used to effectively regenerate a sulfone-containing alkylation catalyst. Additionally, it is necessary to separate ASO from the sulfone in order to reclaim the sulfone for reuse as a catalyst in the alkylation process.

SUMMARY OF THE INVENTION

It is, therefore, an object of this invention to provide a novel process for the regeneration of alkylation catalysts.

A further object of this invention is to provide a process for the removal of ASO from alkylation catalysts containing a sulfone component.

Thus, the process of the present invention relates to the alkylation of olefin hydrocarbons by paraffin hydrocarbons by utilizing a catalyst mixture that includes a sulfone component. A sulfone-containing mixture comprising a sulfone and ASO is mixed with water in an amount effective for forming a hydrous sulfone-containing mixture comprising the two immiscible liquid phases of an ASO phase and a sulfone with water phase wherein the ASO phase comprises ASO and the sulfone with water phase comprises water and a portion of the sulfone component of the sulfone-containing mixture.

Figure 1:
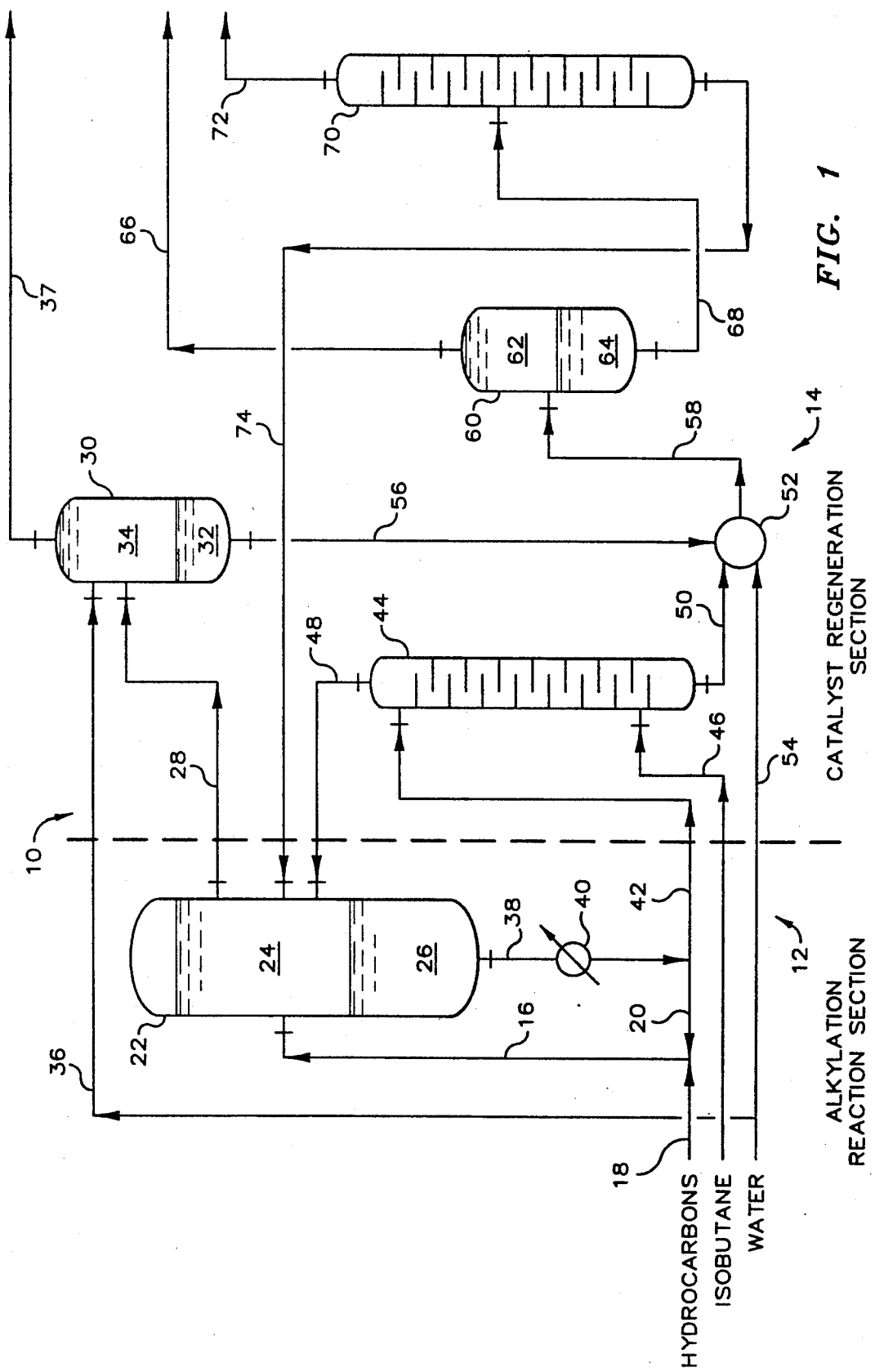
FIG. 1 provides schematic representation of the process which is one embodiment of the invention.

Other objects and advantages of the invention will be apparent from the foregoing detailed description of the invention and the appended claims.

DETAILED DESCRIPTION OF THE INVENTION

The acid soluble oil composition referred to herein is produced as a reaction by-product in an alkylation process comprising the step of contacting a hydrocarbon mixture, which comprises olefins and isoparaffins, with an alkylation catalyst, which comprises, consists of, or consists essentially of a hydrogen halide component and a sulfone component. As referred to within this description and in the claims, the term "acid soluble oil", or "ASO", means those conjunct polymers which are highly olefinic oils produced by acid-catalyzed reactions of hydrocarbons. An extensive description and characterization of certain types of conjunct polymer oils is provided in the *Journal of Chemical and Engineering Data* article entitled "Molecular Structure of Conjunct Polymers", pages 150–160, Volume 8, Number 1, by Miron and Lee. This article is incorporated herein by reference. The physical properties of ASO depend upon the particular hydrocarbon feed processed, the catalyst utilized in the process, feed contaminants such as hydrogen sulfide, butadiene, oxygenates and other compounds, and the alkylation process reaction conditions.

Thus, as the term is more narrowly defined herein, ASO will be those conjunct polymers produced as a by-product in the catalyzed reaction of mono-olefins with isoparaffins utilizing a catalyst mixture comprising, consisting of, or consisting essentially of a sulfone component and a hydrogen halide component. The preferred mono-olefins for use in the catalyzed reaction are those having from three to five carbon atoms and the preferred isoparaffins are those having from four to six carbon atoms. The preferred sulfone component is sulfolane, and the preferred hydrogen halide component is hydrogen fluoride.

The ASO by-product derived from the hydrocarbon reaction catalyzed by a sulfone-containing alkylation catalyst can further be generally characterized as having a specific gravity, with water at 60° F. as the reference, in the range of from about 0.8 to about 1.0, an average molecular weight in the range of from about 250 to about 350, and a bromine number in the range of from about 40 to about 350.

The hydrogen halide component of the catalyst composition or catalyst mixture can be selected from the group of compounds consisting of hydrogen fluoride (HF), hydrogen chloride (HCl), hydrogen bromide (HBr), and mixtures of two or more thereof. The preferred hydrogen halide component, however, is hydrogen fluoride, which can be utilized in the catalyst composition in anhydrous form; but, generally, the hydrogen fluoride component utilized can have a small amount of water. In a catalyst composition including hydrogen fluoride and sulfolane, the amount of water present in no event can be more than about 30 weight percent of the total weight of the hydrogen fluoride component, which includes the water. Preferably, the amount of water present in the hydrogen fluoride component is less than about 10 weight percent. Most preferably, the amount of water present in the hydrogen fluoride component is less than 7 weight percent. When referring herein to the hydrogen halide component, or more specifically to the hydrogen fluoride component, of the catalyst composition of the invention, it should be understood that these terms mean that the hydrogen halide component is either an anhydrous mixture or a non-anhydrous mixture. The references herein to weight percent water contained in the hydrogen halide component means the ratio of the weight of water to the sum weight of the water and hydrogen halide multiplied by a factor of 100 to place the weight ratio in terms of percent.

The sulfones suitable for use in this invention are the sulfones of the general formula

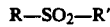

R—SO$_2$—R' wherein R and R' are monovalent hydrocarbon alkyl or aryl substituents, each containing from 1 to 8 carbon atoms. Examples of such substituents include dimethylsulfone, di-n-propylsulfone, diphenylsulfone, ethylmethylsulfone and the alicyclic sulfones wherein the SO$_2$ group is bonded to a hydrocarbon ring. In such a case, R and R' are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethyl-sulfone. These sulfones may advantageously be used in the form of mixtures.

The alkylation catalyst used in the alkylation process wherein an ASO reaction by-product is produced can comprise, consist of, or consist essentially of a hydrogen halide component as described herein and a sulfone component as described herein. Preferably, the ASO by-product will be produced in an alkylation process in which the hydrocarbon mixture is contacted with an alkylation catalyst having sulfolane as its sulfone component and hydrogen fluoride as its hydrogen halide component. In the case where the alkylation catalyst comprises sulfolane and hydrogen fluoride, good alkylation results can be achieved with weight ratio of hydrogen fluoride to sulfolane in the alkylation catalyst in the range of from about 1:1 to about 40:1. A preferred weight ratio of hydrogen fluoride to sulfolane can range from about 2.3:1 to about 19:1; and, more preferably, it can range from 3:1 to 9:1.

In order to improve selectivity of the alkylation reaction of the present invention toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8 to 15. It is emphasized, however, that the above recited ranges for the molar ratio of isoparaffin-to-olefin are those which have been found to be commercially practical operating ranges; but, generally, the greater the isoparaffin-to-olefin ratio in an alkylation reaction, the better the resultant alkylate quality.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 120° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst of the present invention generally should be sufficient to provide for essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40-90 volume percent catalyst phase and about 60-10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

The alkylation process may be carried out either as a batch or continuous type of operation, although it is preferred for economic reasons to carry out the process continuously. It has been generally established that in alkylation processes, the more intimate the contact between the feedstock and the catalyst the better the quality of alkylate product obtained. With this in mind, the present process, when operated as a batch operation, is characterized by the use of vigorous mechanical stirring or shaking of the reactants and catalyst.

In continuous operations, in one embodiment, reactants can be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. As described herein, a portion of the catalyst can be continuously regenerated or reactivated by any suitable treatment and returned to the alkylation reactor.

This invention includes a process for removing ASO from a mixture containing a sulfone compound and a concentration of ASO. Generally, the sulfone-containing mixture is in the form of a single liquid phase which comprises a sulfone component and ASO. The process includes the step of mixing or contacting water with the sulfone-containing mixture, comprising a sulfone component and ASO, to form a hydrous sulfone-containing mixture. Any means or method can be used which suitably provides for the mixing or contacting of water with the sulfone-containing mixture to produce the hydrous sulfone-containing mixture. The hydrous sulfone-containing mixture includes at least two intimately mixed, immiscible, liquid phases including, but not necessarily limited to, an ASO phase and a sulfone with water phase. The immiscible liquid phases of the hydrous sulfone-containing mixture can subsequently be separated into their respective phases. Any means or method can be used which suitably provides for the separating of the ASO phase from the sulfone with water phase.

When mixing or contacting water with the sulfone-containing mixture, any apparatus suitable for providing intimate mixing or contact can be used such as flow or line mixers and mechanically agitated vessels. Examples of flow or line type mixers include jet mixers, injectors, orifices, mixing nozzles, valves, pumps, agitated line mixers, packed tubes, pipe lines and the like. The mechanically agitated vessels include such devices as vessels equipped with propellers or impellers utilized to accomplish mixing and dispersion. It is generally desirable to use a continuous type process whereby the water is continuously mixed with the sulfone-containing mixture followed by a separation of the resultant ASO phase and sulfone with water phase by any means or method which suitably provides for separating the at least two immiscible liquid phases including the ASO phase and sulfone with water phase. In the continuous process, it is common for the mixing or contacting step to be performed separately, and by a separate apparatus, from that of the separating step. Flow or line mixers provide suitable means for mixing in a continuous process. The mixing and separating steps can also be conducted in a batchwise fashion usually in a single vessel which defines both a mixing zone and a separation zone. Mechanically agitated vessels can be utilized as apparatus to permit the batchwise mixing of water and the sulfone-containing mixture and separating of the resulting ASO and sulfone with water phases. As for the separation of the immiscible liquid phases, a vessel, which defines a separation zone, can suitably be used; provided, it has the appropriate volume to permit the separation of the immiscible fluids by gravity or any other appropriate means. Other mechanical devices, such as, for example, centrifuges, can be used to perform the separation of the immiscible phases.

Any amount of water relative to the quantity of the sulfone-containing mixture can be utilized in the process provided that the amount of water mixed with the sulfone-containing mixture is sufficient for causing the subsequent formation of at least two immiscible, liquid phases including an ASO phase and a sulfone with water phase. The ASO phase can comprise ASO, and the sulfone with water phase can comprise water and at least a portion of the sulfone component contained in the sulfone-containing mixture. Generally, it is desirable to mix an amount of water with the sulfone-containing mixture such that the volumetric ratio of the sulfone component to water component in the hydrous sulfone-containing mixture is in the range of from about 6:1 to about 1:6; but, preferably, the volumetric ratio of sulfone to water in the hydrous sulfone-containing mixture can be in the range of from about 3:1 to about 1:3; and, most preferably, the volumetric ratio can be in the range of from 3:2 to 1:1.

The ASO phase of the hydrous sulfone-containing mixture can generally represent from about 1 to about 75 volume percent of the mixture. But, preferably, the volume percent of the hydrous sulfone-containing mixture constituting its ASO phase is in the range of from about 5 to about 50; and, most preferably, the volume percent can range from 10 to 30 of the hydrous sulfone-containing mixture. The ASO phase, when allowed to separate from the sulfone with water phase, will predominantly comprise ASO and can also include lesser fractional quantities of water and sulfone. Generally, the volumetric percent of ASO in the ASO phase can be greater than about 80; but, preferably, the ASO will represent more than about 90 volume percent of the ASO phase. Most preferably, the ASO will constitute more than 95 volume percent of the ASO phase. Because it is impractical for the process to yield an ASO phase that is 100 percent ASO, the upper concentration limit of ASO in the ASO phase will approximate about 99 volume percent. Thus, the concentration range of ASO in the ASO phase will generally be in the range of from about 80 to about 99 volume percent, preferably from about 90 to about 99 volume percent, and most preferably from 95 to 99 volume percent.

The components which can comprise the ASO phase, in addition to the ASO, include water and a sulfone. The concentration of water in the ASO phase in most instances will be less than 15 volume percent and generally in the range of from about 0.01 to about 15 volume percent of the ASO phase. Preferably, the water concentration will be in the range of from about 0.1 to about 5 volume percent of the ASO phase; and, most preferably, it will be in the range of from 0.1 to 3 volume percent of the ASO phase. As for the sulfone concentration of the ASO phase, in most instances, it will be less than about 15 volume percent, therefore, being in the range upwardly to about 15 volume percent. Preferably, the concentration of sulfone in the ASO phase can range from about 0.5 to about 8 volume percent; and, most preferably, the sulfone concentration in the ASO phase can range from 1 to 5 volume percent.

The sulfone with water phase can comprise water and at least a portion of the sulfone contained in the sulfone-containing mixture. To have the most effective process, however, it is desirable for a major portion of the sulfone component of the sulfone-containing mixture to be recovered in the sulfone with water phase; thus, in most instances, the fraction of the sulfone contained in the sulfone-containing mixture that can be recovered in the sulfone with water phase can exceed about 50 volume percent. Preferably, the amount of sulfone recovered can exceed about 60 volume percent; and, most preferably, the amount recovered will exceed 75 volume percent. While it is desirable to minimize the concentration of ASO in the sulfone with water phase, in many instances, there can be a small concentration of ASO in the sulfone with water phase. Generally, however, the concentration of ASO in the sulfone with water phase can be less than about 20 volume percent, preferably, less than about 10 volume percent, and most preferably, less than 5 volume percent.

The process conditions under which the water and sulfone-containing mixture can be mixed or contacted include mixing or contacting temperatures in the range of from about 0° F. to about 250° F., with 40° F. to 260° F. being preferred. The mixing or contacting pressures include those within the range of from about 0.5 atmospheres of absolute pressure to about 30 atmospheres of absolute pressure, with 0.95 atmospheres of absolute pressure to 25 atmospheres of absolute pressure being preferred. As for the process conditions under which the ASO phase and sulfone with water phase are separated, the separating temperature can range from about 0° F. to about 250° F., with 40° F. to 260° F. being preferred. The separating pressures can range from about 0.5 atmospheres of absolute pressure to about 30 atmospheres of absolute pressure with preferred separating pressures being in the range of from 0.95 atmospheres of absolute pressure to 25 atmospheres of absolute pressure.

The sulfone with water phase can further be processed to remove at least a portion of the water contained therein by any means suitable for removing or separating water from the sulfone with water phase to thereby form a remaining portion of the sulfone with water phase. For the best performance of the process, it is advantageous to remove a substantial portion of the water contained in the sulfone with water phase to produce the remaining portion of sulfone with water phase having a concentration of water of less than about 5 volume percent, but preferably, less than about 3 volume percent. Thus, the process step for separating at least a portion of the water contained in the sulfone with water phase will produce two streams: a water stream having at least a portion, and preferably a significant portion, of the water contained in the sulfone with water phase and the stream constituting the remaining portion of the sulfone with water phase. The sulfone with water phase after having a portion of the water removed, or preferably a significant portion of the water removed, can be utilized as at least a portion of the sulfone component of the sulfone-containing alkylation catalyst as earlier described herein.

This invention contemplates the resolution of problems associated with the regeneration of sulfone-containing alkylation catalyst mixtures by the removal of at least a portion of the ASO contained within such mixtures. The accumulation of ASO in sulfone-containing alkylation catalysts occurs when an alkylation process continuously reuses its catalyst. In a continuous alkylation process, the ASO reaction by-product will build up in the catalyst until, if not removed, it reaches unacceptable concentration levels that can have negative effects upon the catalyst performance and, ultimately, the alkylation product quality. It is generally desirable to maintain the concentration of ASO in the sulfone-containing alkylation catalyst at no more than about 20 weight percent of the catalyst with the weight percent ASO being based upon the total weight of the catalyst mixture exclusive of the ASO component. Preferably, the concentration of the ASO in the sulfone-containing alkylation catalyst is less than about 15 weight percent, and most preferably, the concentration of ASO is less than 10 weight percent. There may be some process advantages in maintaining a low concentration of ASO in the sulfone-containing catalyst mixture, but it is believed that an ASO concentration exceeding about 10 weight percent of the catalyst will have a detrimental effect upon the catalyst performance. Thus, in order to maintain the catalytic activity of a sulfone-containing alkylation catalyst mixture, the catalyst must be processed to remove at least a portion of the ASO contained within such catalyst mixture.

It is desirable, however, for the hydrogen halide component of the ASO contaminated sulfone-containing alkylation catalyst mixture to be minimized before mixing or contacting the resultant sulfone-containing mixture with water to induce the formation of at least two immiscible liquid phases. In particular, when a significant portion of the sulfone-containing alkylation catalyst mixture comprises hydrogen halide; for instance, when the weight ratio of hydrogen halide to sulfolane is in the range of from about 1:1 to about 40:1, it is preferable for a major portion of the hydrogen halide to be removed from the catalyst mixture to give the sulfone-containing mixture or a recovered catalyst mixture. This sulfone-containing mixture or recovered catalyst mixture can comprise, consist of, or consist essentially of a sulfone component, a hydrogen halide component, and ASO. Generally, the concentration of the hydrogen halide component in the recovered catalyst mixture will be less than about 10 weight percent of the catalyst mixture with the weight percent determined by the weight fraction of the hydrogen halide to total weight of hydrogen halide and sulfone multiplied by a factor of 100 to yield a percent. Because it is very difficult to remove the entire amount of hydrogen halide from the catalyst mixture, the lower limit of hydrogen halide concentration can approach about 1.0 weight percent, but, preferably, the lower concentration limit of hydrogen halide can be less than 0.1 weight percent. Thus, the concentration range of hydrogen halide in the recovered catalyst mixture can range from about 0.1 weight percent to about 10 weight percent. Preferably, however, the concentration can range from about 0.1 to about 7.5 weight percent, and most preferably, it can range from 0.1 to 5.0 weight percent.

Now referring to FIG. 1, there is depicted by schematic representation a process 10 which includes an alkylation reaction section 12 and a catalyst regeneration section 14. A hydrocarbon feed mixture, comprising olefins and isoparaffins, is introduced into riser-reactor 16 through conduit 18. Riser-reactor 16 defines a reaction zone wherein the hydrocarbon feed mixture is contacted, or admixed, with a sulfone-containing alkylation catalyst, which comprises sulfolane and hydrogen fluoride, to thereby produce an alkylation reaction mixture comprising an alkylate product, ASO and the sulfone-containing alkylation catalyst. The olefins of the hydrocarbon feed mixture generally comprise one or more olefins having from three to five carbon atoms, and the isoparaffins of the hydrocarbon feed mixture generally will have from four to six carbon atoms. The sulfone-containing alkylation catalyst is introduced into riser-reactor 16 via conduit 20. The admixture of hydrocarbon feed mixture and sulfone-containing alkylation catalyst passes through the reaction zone defined by riser-reactor 16 wherein a reaction takes place in which the olefins of the hydrocarbon feed mixture react with isoparaffins of the hydrocarbon feed mixture to produce the alkylate product. Also, within the reaction zone, the reaction by-product, ASO, is formed. The alkylation reaction mixture, or reaction effluent, from riser-reactor 16 passes to settler vessel 22, which defines a separation zone for separating the alkylate product from the alkylation reaction mixture to produce a separated reaction product 24 and a separated sulfone-containing alkylation catalyst 26. The separated sulfone-containing alkylation catalyst will contain a substantial amount, or that amount that is not soluble in the separated reaction product, of the alkylation reaction by-product, ASO. The separated reaction product 24 passes downstream via conduit 28 to phase separator 30 wherein the separated reaction product is contacted with water and wherein a phase separation is induced. Thus, phase separator 30 defines a contacting zone for contacting the separated reaction product with water and a separation zone for forming and separating a water phase 32, which comprises water, and a hydrocarbon phase 34, which comprises hydrocarbons. Water is introduced into phase separator 30 via conduit 36, and hydrocarbon phase 34 passes to downstream processing by way of conduit 37. The separated sulfone-containing alkylation catalyst 26 can be recycled via conduits 38 and 20 to riser-reactor 16 for reuse as the sulfone-containing alkylation catalyst. Interposed in conduit 38 is catalyst cooler 40, which defines a heat transfer zone for exchanging heat from separated sulfone-containing alkylation catalyst 26 to a heat transfer fluid such as water.

At least a portion, sometimes referred to as a slip stream or a drag stream, of the separated sulfone-containing alkylation catalyst 26 passes by way of conduit 42 to stripping column 44, which defines a separation zone for separating the slip stream of separated sulfone-containing alkylation catalyst into an overhead stream, or hydrogen fluoride stream, comprising a major portion of the hydrogen fluoride contained in the slip stream, and a bottoms stream, comprising a major portion of the sulfone component of the slip stream. The bottoms stream will also contain a major portion of the reaction by-product, ASO, contained in the slip stream. Introduced by way of conduit 46 is vaporous isobutane for stripping the hydrogen fluoride from the slip stream. The overhead stream passes by way of conduit 48 to settler vessel 22 wherein substantially all of hydrogen fluoride is recombined for reuse with the separated sulfone-containing alkylation catalyst 26, and substantially all of the stripping isobutane is combined with the separated reaction product 24.

The bottoms stream from stripping column 44 passes by way of conduit 50 to mixing means 52, which defines a mixing zone for mixing the bottoms stream with water to thereby form a hydrous sulfone-containing mixture which can subsequently form separate, immiscible ASO and sulfolane with water phases. Water is provided to the mixing zone defined by mixing means 52 through conduit 54. The water phase 32 can also optionally be injected into the mixing zone defined by mixing means 52 via conduit 56. The resultant hydrous sulfone-containing mixture then passes by way of conduit 58 to phase separator 60, which defines a separation zone for separating the hydrous sulfone-containing mixture into an ASO phase 62, comprising ASO, and a sulfolane with water phase 64, comprising sulfolane and water. The ASO phase 62 passes to downstream processing via conduit 66, and the sulfolane with water phase 64 passes by way of conduit 68 to fractionator 70. Fractionator 70 defines a separation zone and provides means for separating at least a portion of the water contained in sulfolane with water phase 64 to form a remaining portion of the sulfolane with water phase 64. The separated water passes from fractionator 70 via conduit 72 to downstream processing. The remaining portion of the sulfolane with water phase 64 passes from fractionator 70 by way of conduit 74 to settler vessel 22 wherein it is combined with the separated sulfone-containing alkylation catalyst.

The following example demonstrates the advantages of the present invention. These examples are by way of illustration only, and are not intended as limitations upon the invention as set out in the appended claims.

EXAMPLE I

This example illustrates the advantages of utilizing water as an extraction solvent for removing sulfolane from a sulfolane and ASO mixture. As demonstrated by the data presented in Table I, using water as an extraction liquid is very effective for separating ASO from sulfolane. Table I shows for various experimental runs the volume fraction of each of the three components of a mixture and the composition of the resultant immiscible phases. As can be seen from the data presented, the toph phase is predominantly ASO and the bottom phase is predominantly sulfolane and water with only a minor concentration of ASO.

Each of the experimental runs was conducted in a 100 mL volumetric cylinder. The appropriate amount of each component, calculated by multiplying the mole fraction given in Table I by 100 mL, was added to the cylinder. The cylinder was then shaken vigorously for 30 seconds and allowed to stand for 2 hours. The volumes of the resulting liquid phases were then read from the cylinder's graduations. Samples of each phase were taken with a syringe and submitted for analysis, the results of which are provided in Table I.

TABLE I

| Run No. | Vol. Fraction ASO | Vol. Fraction Sulf. | Vol. Fraction H2O | Tertiary Phase Diagram ASO/Sulfolane/Water Top Phase % Vol | % C | % H | % S | % ASO | % Sulf. | % H2O | Bottom Phase % Vol | % C | % H | % S | % Sulf. |
|---|---|---|---|---|---|---|---|---|---|---|---|---|---|---|---|
| 1 | 0.25 | 0.75 | 0.00 | 25.0 | 75.50 | 10.50 | 5.00 | 80.84 | 18.74 | 0.420 | 75.0 | 43.40 | 6.80 | 25.50 | 95.58 |
| 2 | 0.75 | 0.00 | 0.25 | 75.5 | 86.80 | 12.00 | 0.68 | 97.14 | 2.55 | 0.310 | 24.5 | 0.18 | 9.60 | 0.00 | 0.00 |
| 3 | 0.25 | 0.00 | 0.75 | 25.0 | 86.80 | 11.30 | 0.46 | 96.27 | 1.72 | 2.010 | 75.0 | 0.10 | 11.00 | 0.00 | 0.00 |
| 4 | 0.75 | 0.25 | 0.00 | 74.1 | 86.90 | 11.40 | 0.89 | 96.65 | 3.34 | 0.015 | 25.9 | 40.50 | 6.70 | 25.90 | 97.08 |
| 5 | 0.50 | 0.50 | 0.00 | 48.2 | 86.40 | 11.30 | 0.94 | 96.47 | 3.52 | 0.009 | 51.8 | 40.30 | 6.60 | 18.30 | 68.59 |
| 6 | 0.50 | 0.00 | 0.50 | 49.1 | 86.60 | 11.40 | 0.67 | 97.22 | 2.51 | 0.270 | 50.9 | 0.09 | 3.20 | 0.00 | 0.00 |
| 7 | 0.20 | 0.20 | 0.60 | 21.1 | 86.00 | 11.20 | 0.63 | 97.56 | 2.36 | 0.074 | 78.9 | 12.00 | 9.80 | 8.40 | 2.00 |
| 8 | 0.60 | 0.20 | 0.20 | 57.4 | 86.30 | 11.40 | 0.67 | 97.48 | 2.51 | 0.009 | 42.6 | 22.80 | 8.40 | 15.40 | 57.72 |
| 9 | 0.20 | 0.60 | 0.20 | 22.4 | 84.10 | 11.10 | 1.32 | 94.38 | 4.95 | 0.670 | 77.6 | 32.40 | 7.80 | 21.50 | 80.59 |
| 10 | 0.25 | 0.25 | 0.50 | 22.2 | 86.40 | 11.10 | 0.70 | 97.36 | 2.62 | 0.016 | 77.8 | 15.60 | 8.00 | 10.60 | 39.73 |
| 11 | 0.50 | 0.25 | 0.25 | 47.2 | 86.30 | 11.70 | 0.71 | 95.46 | 2.66 | 1.880 | 52.8 | 23.00 | 8.30 | 15.70 | 58.85 |
| 12 | 0.25 | 0.50 | 0.25 | 25.0 | 87.60 | 11.50 | 0.64 | 87.95 | 2.40 | 9.650 | 75.0 | 39.40 | 8.00 | 20.90 | 78.34 |
| 13 | 0.30 | 0.30 | 0.40 | 30.4 | 87.00 | 11.30 | 1.10 | 95.73 | 4.12 | 0.150 | 69.6 | 20.70 | 8.90 | 13.90 | 52.10 |
| 14 | 0.40 | 0.30 | 0.30 | 38.2 | 86.30 | 11.40 | 0.72 | 97.23 | 2.70 | 0.069 | 61.8 | 22.30 | 7.50 | 17.10 | 64.09 |
| 15 | 0.30 | 0.40 | 0.30 | 29.1 | 86.10 | 11.00 | 0.75 | 97.18 | 2.81 | 0.005 | 70.9 | 25.30 | 7.30 | 19.50 | 73.09 |
| 16 | 0.30 | 0.10 | 0.60 | 29.8 | 86.80 | 11.20 | 0.99 | 93.29 | 3.71 | 3.000 | 70.2 | 10.40 | 1.30 | 6.50 | 24.36 |
| 17 | 0.60 | 0.30 | 0.10 | 58.2 | 86.20 | 11.60 | 0.91 | 96.45 | 3.41 | 0.140 | 41.8 | 32.90 | 7.20 | 23.50 | 88.08 |
| 18 | 0.10 | 0.60 | 0.30 | 10.7 | 74.10 | 10.20 | 3.80 | 85.23 | 14.24 | 0.530 | 89.3 | 29.40 | 8.00 | 20.20 | 75.71 |
| 19 | 0.30 | 0.20 | 0.50 | 29.1 | 87.20 | 11.40 | 0.60 | 82.95 | 2.25 | 14.800 | 70.9 | 11.90 | 6.50 | 7.10 | 26.61 |
| 20 | 0.50 | 0.30 | 0.20 | 45.3 | 83.70 | 11.60 | 1.60 | 89.42 | 6.00 | 4.580 | 54.7 | 20.50 | 6.00 | 15.70 | 58.85 |
| 21 | 0.20 | 0.50 | 0.30 | 21.4 | 85.80 | 11.60 | 0.99 | 96.26 | 3.71 | 0.028 | 78.6 | 27.90 | 6.90 | 20.10 | 75.34 |

While this invention has been described in terms of the presently preferred embodiment, reasonable variations and modifications are possible by those skilled in the art. Such variations and modifications are within the scope of the described invention and the appended claims.

What which is claimed is:

1. A process for removing acid soluble oil (ASO) from a sulfone-containing mixture containing a sulfone component and ASO, said process comprising the step of:
   mixing water with said sulfone-containing mixture to form a hydrous sulfone-containing mixture wherein an amount of water mixed with said sulfone-containing mixture is effective for causing the subsequent formation of an ASO phase and a sulfone with water phase wherein said ASO phase comprises ASO and said sulfone with water phase comprises water and at least a portion of said sulfone component.

2. A process as recited in claim 1, wherein said amount of water mixed with said sulfone-containing mixture is such that the volumetric ratio of the sulfone component to water in said hydrous sulfone-containing mixture is in the range of from about 6:1 to about 1:6.

3. A process as recited in claim 2, further comprising the step of: separating said hydrous sulfone-containing mixture into said ASO phase and said sulfone with water phase.

4. A process as recited in claim 3, wherein said ASO phase represents from about 1 to about 75 volume percent of said hydrous sulfone-containing mixture.

5. A process as recited in claim 4, wherein an amount of water contained in said ASO phase is in the range of from about 0.01 to about 15 volume percent of said ASO phase.

6. A process as recited in claim 5, wherein an amount of sulfone contained in said ASO phase is in the range upwardly to about 15 volume percent of said ASO phase.

7. A process as recited in claim 6, wherein an amount of ASO contained in said ASO phase is in the range of from about 80 volume percent to about 99 volume percent of said ASO phase.

8. A process as recited in claim 7, wherein said sulfone component comprises sulfolane.

9. A process as recited in claim 8, wherein the temperature of the mixing step is in the range of from about 0° F. to about 250° F., and the pressure of the mixing step is in the range of from about 0.5 atmospheres of absolute pressure to about 30 atmospheres of absolute pressure.

10. A process as recited in claim 9, wherein the temperature of the separating step is is in the range of from about 0° F. to about 250° F. and the pressure of the separating step is in the range of from about 0.5 atmospheres of absolute pressure to about 30 atmospheres of absolute pressure.

11. A process comprising: mixing a sulfolane-containing mixture comprising sulfolane and acid soluble oil (ASO) with water to thereby form an ASO phase and a sulfolane with water phase wherein said ASO phase comprises ASO and said sulfolane with water phase comprises sulfolane and water.

12. A process as recited in claim 11, further comprising: separating said ASO phase from said sulfolane with water phase.

13. A process as recited in claim 12, further comprising: separating at least a portion of the water contained in said sulfolane with water phase to form a water stream and a remaining portion of said sulfolane with water phase.

14. A process as recited in claim 13, further comprising:
   utilizing said remaining portion of said sulfolane with water phase as at least a portion of a sulfolane-containing alkylation catalyst wherein said sulfolane-containing alkylation catalyst comprises sulfolane and hydrogen fluoride; and
   contacting a hydrocarbon mixture, comprising olefins and isoparaffins, with said sulfolane-containing alkylation catalyst within a reaction zone to thereby produce an alkylation reaction mixture comprising an alkylate product, ASO, and said sulfolane-containing alkylation catalyst.

15. A process as recited in claim 14, further comprising:
separating said alkylate product from said alkylation reaction mixture within a first separation zone to produce a separated reaction product and a separated sulfolane-containing alkylation catalyst wherein said separated reaction product comprises at least a portion of said alkylate product and said separated sulfolane-containing alkylation catalyst comprising at least a portion of the ASO produced by said contacting step; and
optionally utilizing said separated sulfolane-containing alkylation catalyst as at least a portion of said sulfolane-containing alkylation catalyst.

16. A process as recited in claim 15, further comprising: separating at least a portion of said separated sulfolane-containing alkylation catalyst into a hydrogen fluoride stream comprising hydrogen fluoride and said sulfolane-containing mixture.

17. A process as recited in claim 16, further comprising: utilizing said hydrogen fluoride streams as at least a portion of said sulfolane-containing alkylation catalyst.

18. A process as recited in claim 17, further comprising:
contacting said separated reaction product with water within a second separation zone;
forming a water phase and a hydrocarbon phase; and
optionally utilizing said water phase as at least a portion of the water used in the mixing step.

19. A process for removing acid soluble oil (ASO) from a sulfolane-containing mixture, said process comprising the steps of:
mixing water with said sulfolane-containing mixture in an amount such that the volumetric ratio of sulfolane to water in a resultant hydrous sulfolane-containing mixture is in the range of from about 6:1 to about 1:6; and
thereafter, separating said resultant hydrous sulfolane-containing mixture into an ASO phase representing from about 1 to about 75 volume percent of said resultant hydrous sulfolane-containing mixture and a sulfolane with water phase, said ASO phase comprising water in the range of from about 0.01 to about 15 volume percent of said ASO phase, sulfolane in an amount upwardly to about 15 volume percent of said ASO phase, and ASO in the range of from about 80 to about 99 volume percent of said ASO phase.

* * * * *